United States Patent
Van De Kerkhof et al.

[11] Patent Number: 6,152,914
[45] Date of Patent: Nov. 28, 2000

[54] CATHETER HAVING A MULTIPLE LOCKING MECHANISM

[75] Inventors: Bart Van De Kerkhof, Zoersel, Belgium; Leo Kretzers, Sittard, Netherlands; Vincent Larik, Landgraaf, Netherlands; Michel Verhoeven, Maastricht, Netherlands

[73] Assignee: Medtronic, Inc., Minneapolis, Minn.

[21] Appl. No.: 09/235,169

[22] Filed: Jan. 22, 1999

[51] Int. Cl.[7] .......................... A61M 25/16; A61M 25/18; A61M 39/00; A61M 39/10
[52] U.S. Cl. ............................................. 604/533
[58] Field of Search ..................... 604/533, 534, 604/535, 538, 539, 905, 530, 531, 532, 264, 523, 96; 285/92

[56] References Cited

U.S. PATENT DOCUMENTS

| | | |
|---|---|---|
| 4,402,319 | 9/1983 | Handa et al. . |
| 4,792,163 | 12/1988 | Kulle ........................................ 285/88 |
| 5,549,554 | 8/1996 | Miraki ..................................... 604/533 |
| 5,558,643 | 9/1996 | Samson et al. .......................... 604/96 |
| 5,586,790 | 12/1996 | Bynum .................................... 285/89 |
| 5,632,754 | 5/1997 | Farley et al. ........................... 606/159 |

*Primary Examiner*—Wynn Wood Coggins
*Assistant Examiner*—Ann T. Lam
*Attorney, Agent, or Firm*—Thomas F. Woods; Michael J. Jaro; Harold Patton

[57] ABSTRACT

A catheter having a multiple locking mechanism for connecting a proximal portion of the catheter shaft to a distal portion of the catheter shaft is provided. Also provided is a method for connecting a catheter shaft employing the multiple locking mechanism of the invention. The multiple locking mechanism permits a proximal shaft to be joined with a distal end portions, while simultaneously ensuring integrity of the connection between the proximal shaft and the distal end portion.

20 Claims, 4 Drawing Sheets

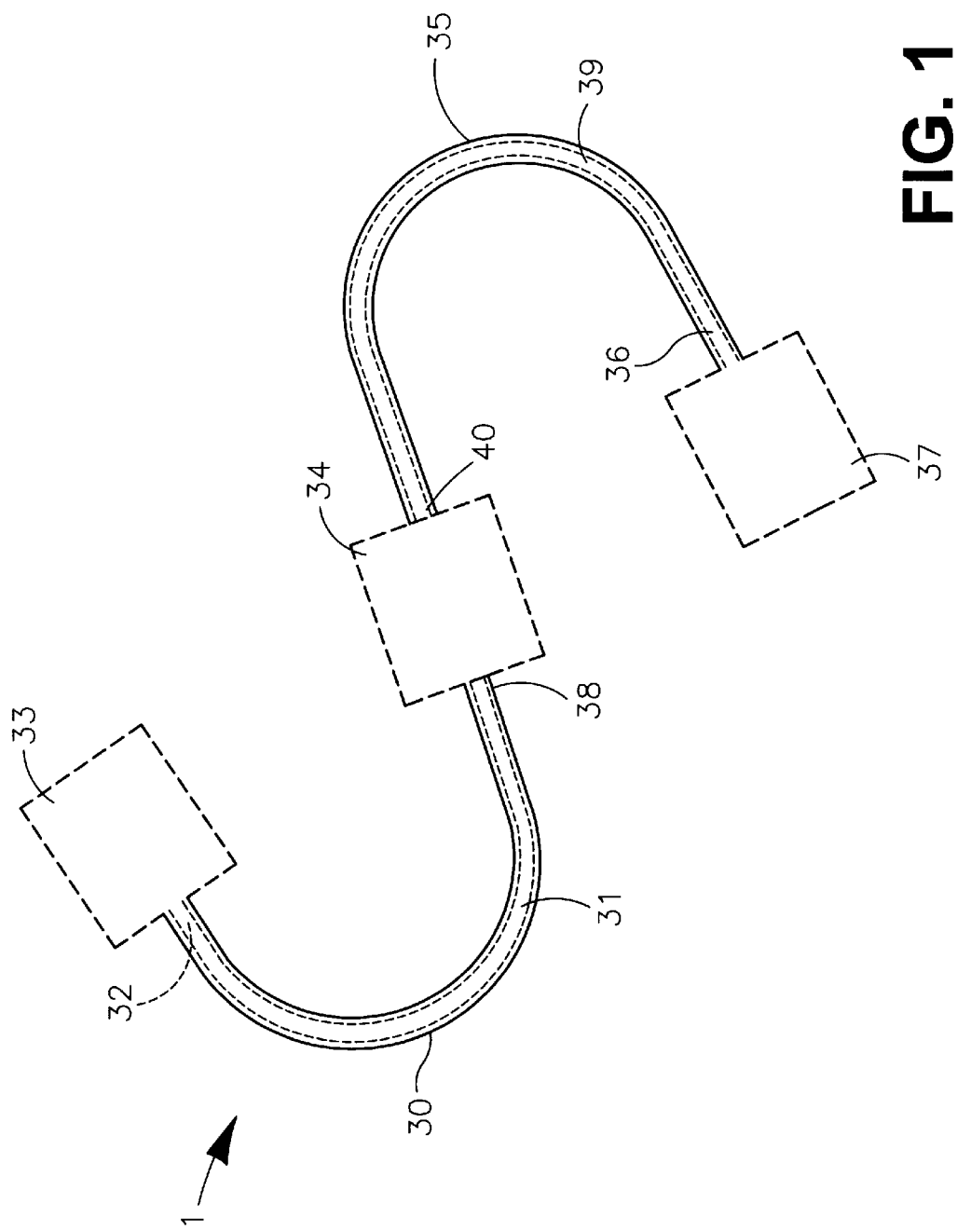

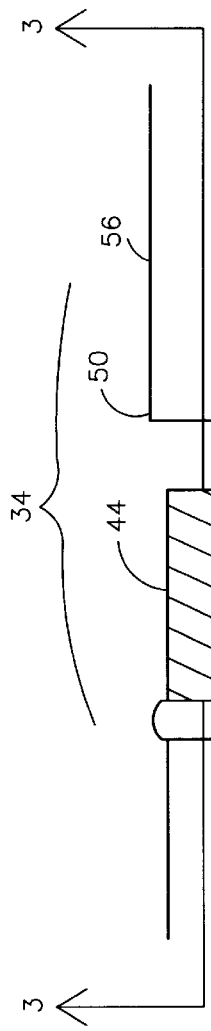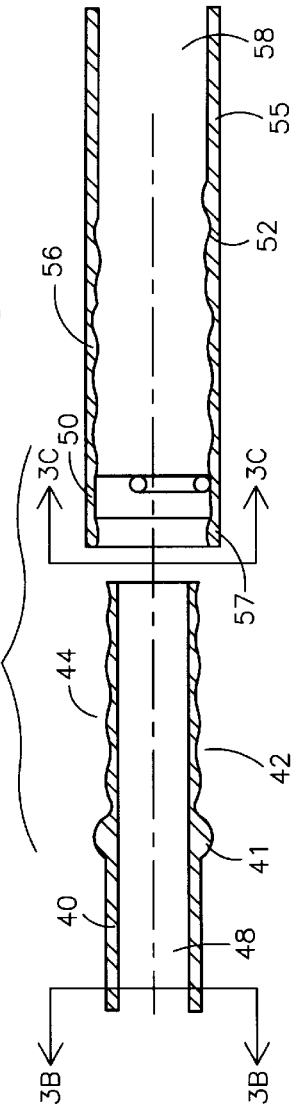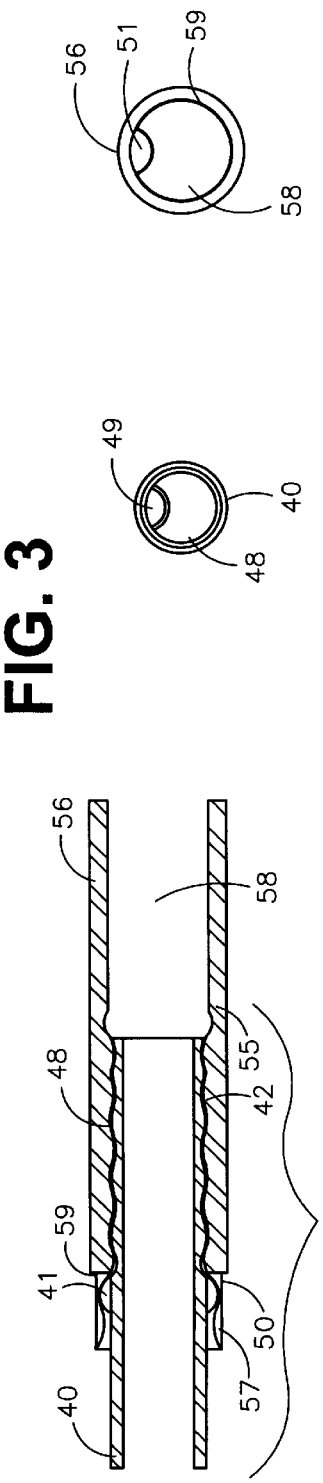

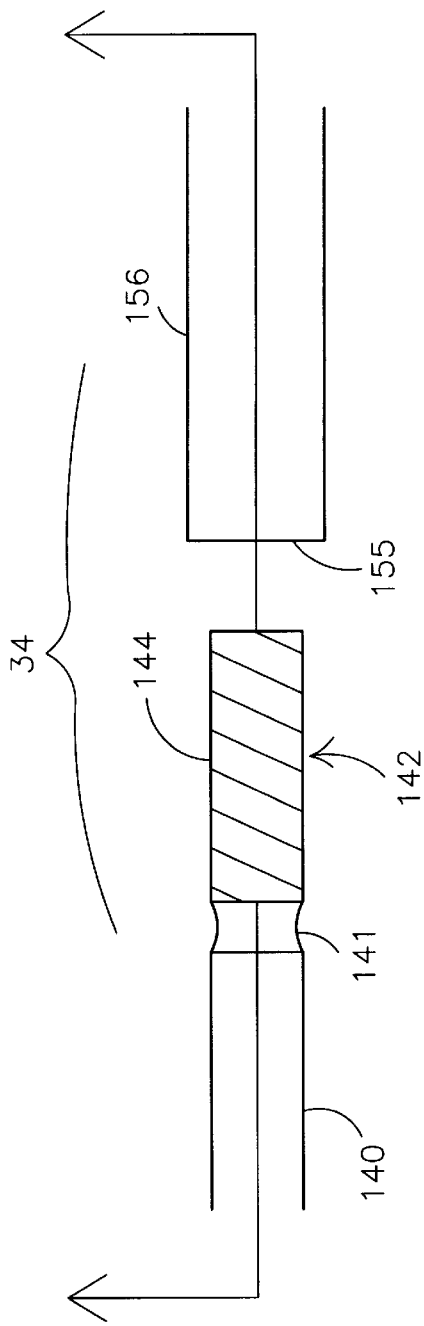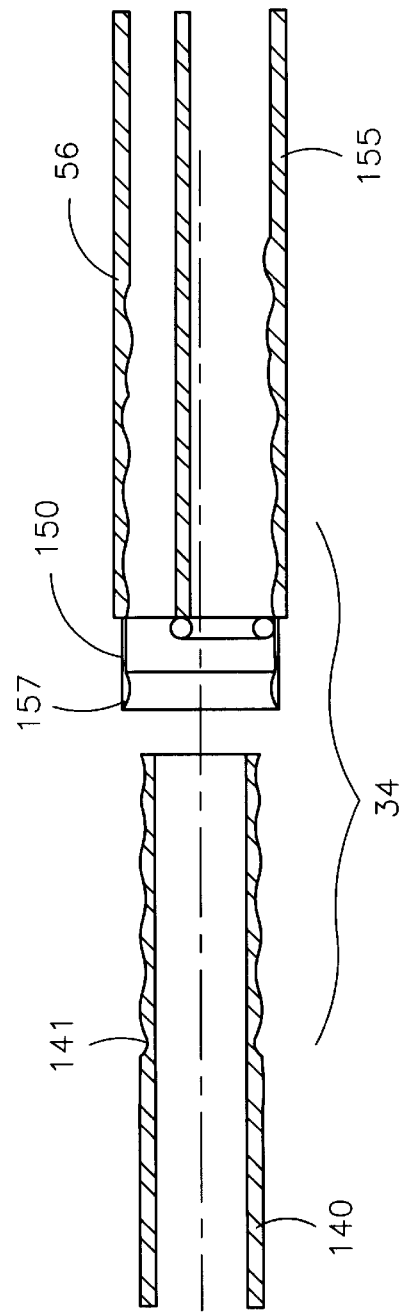

CATHETER HAVING A MULTIPLE LOCKING MECHANISM

FIELD OF INVENTION

The present invention relates to the construction and use of intravascular and other catheters. More particularly, the invention relates to a catheter having a multiple locking mechanism connecting a proximal portion of the catheter shaft to a distal portion of the catheter shaft.

BACKGROUND OF THE INVENTION

Stenosis is a narrowing or constriction of a duct or canal. A variety of disease processes, such as atherosclerotic lesions, immunological reactions, congenital abnormalities, and the like, can lead to stenosis of arteries or ducts. In the case of stenosis of a coronary artery, this typically leads to myocardial ischema.

Atherosclerosis, also known as arteriosclerosis, is a common human ailment arising from the deposition of fat-like substances, referred to as atheroma or plaque, on the walls of blood vessels. Such deposits occur both in peripheral blood vessels that feed the limbs of the body and in coronary blood vessels that feed the heart. When deposits accumulate in localized regions of a blood vessel, the regions become stenosed, blood flow is restricted, and the person's health is at serious risk.

Numerous approaches using catheters for reducing and removing such stenotic deposits have been proposed, including balloon angioplasty, where a balloon-tipped catheter is used to dilate the stenosed region, atherectomy, where a blade or other cutting element is used to sever and remove stenotic material, and laser angioplasty, where laser energy is used to ablate at least a portion of the stenotic material.

Several different types of entirely disposable dilatation catheters are currently employed and may be generally classified based upon their interaction with a guidewire. Although these disposable catheter designs have proven effective under a variety of conditions, their disposability and specific functionality limit the capacity of the surgeon to adapt to changing or unexpected situations. This may increase the costs associated with their use as several different catheters may be necessary to accomplish a simple procedure. For example, it is often necessary to exchange entire catheters during angioplasty procedures. The catheter exchange may be required for any one of several reasons including catheter balloon malfunction, the inability of the specific balloon size to adequately dilate the vascular stenoses, or the need to insert an additional device to remove vascular material. In each of these situations the original dilatation catheter must be removed and a new catheter inserted. It is estimated that about half of the angioplasty procedures require the use of more than one dilatation catheter. Presently, all of the catheters used during such procedures are discarded after a single use.

For these and other reasons, re-useable catheter designs are desired of the type in which the catheter permits uncomplicated modification of components and catheter configuration. Although some "rapid exchange" catheters have been designed to allow for a reusable proximal end combined with a disposable distal end by employing a "locking mechanism," these locking mechanisms are sometimes deficient. For example, U.S. Pat. No. 5,549,554 relates to catheter having separable reusable components, and provides one or more releasable connectors for connecting distal portions to a central body instrument portion. Although the substitution or modification of catheter components is possible through the releasable connectors, the connectors include only a single locking mechanism. Failure of that single mechanism during a procedure may have adverse consequences.

Additionally, a locking mechanism described in U. S. Pat. No. 4,792,163, relates to a secondary safety clamp for a medical tube coupling. The secondary safety clamp may prevent accidental separation of a pair of connected tubular members of a sliding member. The secondary safety clamp is an integrally molded piece defining a toothed rack plus a retention member made up of a pair of jaws between which there may be retained a parenteral solution administration set. Although the secondary safety clamp may be suitable for applications relating to medical tube couplings, the secondary clamp affords little flexibility for application in a catheter.

SUMMARY OF THE INVENTION

Thus, it is an object of the present invention to provide a catheter having a unique locking mechanism that provides the catheter with flexibility and appropriate axial stiffness. In particular, the present invention provides a multiple locking mechanism that permits a reusable proximal shaft to be joined with a disposable distal end while simultaneously ensuring integrity of the connection between the proximal shaft and distal end.

Although a variety of catheters are known in the art, such as those described above, catheters having the multiple locking mechanism described herein, permit the reusable proximal catheter shaft to be freely made of costly materials like nitinol without excessive increase in cost, as the proximal catheter shaft can readily be re-used.

One aspect of the invention provides a catheter body for an intravascular catheter that includes a first body portion having a proximal and distal end and a first lumen extending from the proximal end to the distal end; a second body portion having a proximal and distal end and a second lumen extending from the proximal end to the distal end; a multiple locking mechanism having a first threaded connector at the proximal end of the first body portion; a second threaded connector at the distal end of the second body portion, wherein the first and second threaded connectors cooperate to connect the proximal end of the first body portion to the distal end of the second body portion; a first interlocking element at the proximal end of the first body portion; and a second interlocking element at the distal end of the second body portion, wherein the first and second interlocking elements interlock when the first and second threaded connectors connect the first and second body portions together.

In one embodiment, the second body portion of the catheter has a reusable shaft made of a memory shaped metal. Preferably, the memory shaped metal is nitinol. Typically, the first and second lumens are in fluid communication when the first and second body portions are interlocked. As used herein, the term "interlock" means that at least one of the interlocking elements preferably experiences elastic deformation, and possibly plastic deformation, as the interlocking elements are connected to each other. The deformation may also be experienced as the interlocking coupling elements are disconnected.

In another embodiment, the first body portion of the catheter typically has a guidewire lumen extending from the proximal end to the distal end. Similarly, the second body portion has a guidewire lumen that is in fluid communication with the guidewire lumen of the first body portion when the first and second body portions are interlocked, in this embodiment, the intravascular catheter typically includes a sealing ring between the first and second lumens.

In one embodiment of the multiple locking mechanism employed in the intravascular catheter, the first interlocking coupling element includes a raised annular ring and the second interlocking element includes a latching portion.

In another embodiment of the multiple locking mechanism employed in the intravascular catheter, the first interlocking coupling element includes an annular depression and the second interlocking element includes a latching portion.

In yet another embodiment of the multiple locking mechanism employed in the intravascular catheter, the first interlocking coupling element includes a raised annular ring and the second interlocking element includes an annular depression.

Additionally, the intravascular catheter of the invention can include a work element at the distal end of the first body portion. Typically, the work element is an expandable balloon. The proximal assembly of the intravascular catheter may include a perfusion or aspiration source or a source useful in connection with localized drug delivery at the work element.

A further aspect of the invention is a method for connecting a catheter shaft. The method includes providing a catheter of the invention; connecting the first body portion with the second body portion of the catheter by rotatably engaging the first and second threaded connectors; interlocking the first and second interlocking elements; and placing the first and second lumens in fluid communication. When placing the first and second lumens in fluid communication, a sealing ring between the first and second lumens may be employed.

In one embodiment of the multiple locking mechanism employed in the method, the first interlocking coupling element of the catheter has a raised annular ring and the second interlocking element has a latching portion. In this embodiment, when the first and second interlocking elements are interlocked, this results in deflecting at least one of the raised annular ring and the latching portion.

In another embodiment of the multiple locking mechanism employed in the method, the first interlocking coupling element of the catheter has an annular depression and the second interlocking element has a latching portion. In this embodiment, when the first and second interlocking elements are interlocked, this results in deflecting at least one of the annular depression and the latching portion.

In yet another embodiment of the multiple locking mechanism employed in the method, the first interlocking coupling element of the catheter has a raised annular ring and the second interlocking element has an annular depression. In this embodiment, when the first and second interlocking elements are interlocked, this results in deflecting at least one of the raised annular ring and the annular depression.

In the method of the invention, the first and second interlocking elements of the multiple locking mechanism preferably provide axial tension to the first and second threaded connectors when interlocked. Additionally, when a connection or disconnection of the first and second body portions occurs, an outward deflection of the second interlocking element typically occurs. In another aspect of the method of the invention, the catheter of the invention may have a work element attached to the distal end of the first body portion.

BRIEF DESCRIPTION OF THE DRAWINGS

FIG. 1. is a perspective view of a catheter with interchangeable work elements and a multiple locking mechanism in accordance with the principles of the present invention.

FIG. 2. is a side view of an embodiment of the multiple locking mechanism having first and second threaded connectors and first and second interlocking elements.

FIG. 3. is a cross-sectional view of the multiple locking mechanism shown in FIG. 2 taken along line 3—3 in FIG. 2.

FIG. 3A. is a side view of the multiple locking mechanism coupling the first and second body portions of a catheter.

FIG. 3B. is a cross-sectional view of the catheter body of FIG. 2 taken along line 3B—3B in FIG. 3.

FIG. 3C. is an end view of the distal portion of the multiple locking mechanism in the catheter of FIG. 2 taken along line 3C—3C in FIG. 3.

FIG. 4. is a side view of another embodiment of a multiple locking mechanism according to the present invention.

FIG. 5. is a cross-sectional view of the multiple locking mechanism shown in FIG. 4 taken along line 5—5 in FIG. 4.

DETAILED DESCRIPTION OF THE INVENTION

Figure 6:
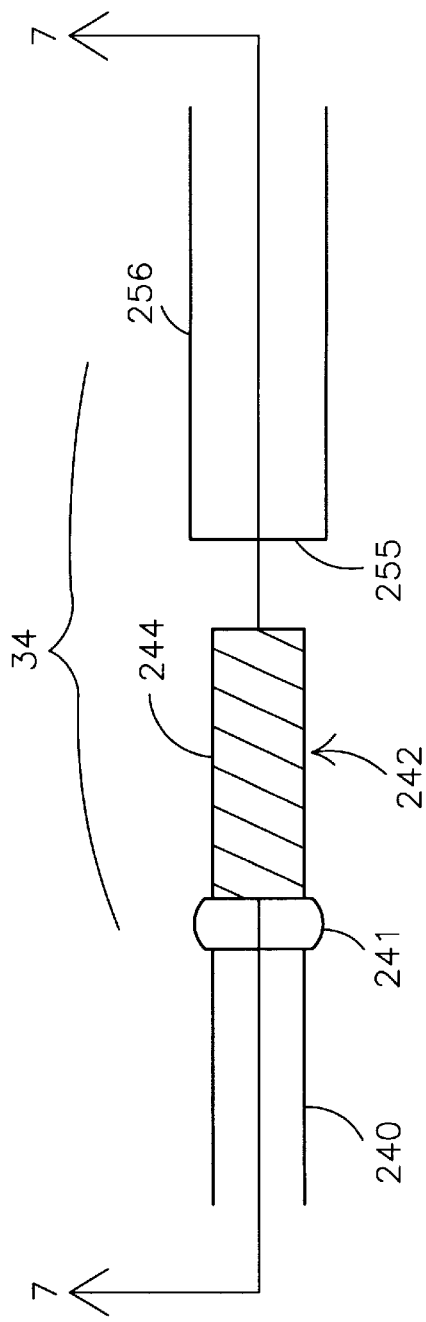
FIG. 6. is a side view of another embodiment of a multiple locking mechanism according to the present invention.

In referring to the drawings, a number of embodiments of a catheter of the present invention will be described. Although several specific embodiments are described herein, these embodiments are merely exemplary and a wide variety of other specific implementations of the present invention may also be accomplished within the scope of this invention.

According to the present invention, a catheter is provided that contains a proximal end, a distal end, and at least one axial lumen therebetween. A multiple locking mechanism is provided for connecting the proximal end to the distal end. As a result, the proximal portion of the catheter shaft may be reused and/or may be employed with a variety of devices on the distal end. Alternatively, the distal portion of the catheter shaft may be re-used and/or may be employed with a variety of devices on the proximal end of the catheter. Although specific embodiments of multiple locking mechanisms are disclosed herein, it should be appreciated by one of skill in the art that a variety of combinations of locking mechanisms are envisioned by the present invention. Further more, although the multiple locking mechanisms disclosed herein include two locking mechanisms, it may be possible to provide catheters connected by three or more locking mechanisms within the scope of the present invention.

Although catheters, in general, are well suited for the treatment of coronary arteries, any body lumen can be treated by a medical device of the present invention, including the vas deferens, ducts of the gallbladder, prostate gland, trachea, bronchus and liver or larger arteries such as the renal and carotid.

Referring to FIG. 1, a catheter of the invention is shown. The catheter has a first body portion 30 and a second body portion 35. The first body portion 30 has a distal end 32, a proximal end 38 and a first lumen 31 that extends from the proximal 38 end to the distal end 32. Similarly, the second body portion 35 has a proximal end 36, a distal end 40 and a second lumen 39 that extends from the proximal end 36 to the distal end 40.

The first body portion 30 and the second body portion 35 may include a variety of different work elements and/or components at their respective distal and proximal ends. For example, a work element 33 is positioned at the distal end 32 of the first body portion 30. Work element 33 is typically a balloon although other work elements 33 may also be employed, including cutters (e.g., a rotablade), grinders, imaging devices, other dilation devices, suction devices, localized drug delivery devices, etc. Likewise, a proximal assembly 37 may be attached to proximal end 36 of the second body portion 35. The proximal assembly 37 can include, for example, a perfusion or aspiration source or any device useful in combination with the work element 33 located at the distal end 32 of the first body portion 30.

The first body portion 30 and second the second body portion 35 are connected using a multiple locking mechanism 34 of the invention. Multiple locking mechanism 34 is connected at the proximal end 38 of the first body portion 30 and further connected at the distal end 40 of the second body portion 35. The multiple locking mechanism 34 includes at least two locking or connection mechanisms. In the illustrative embodiments presented below, the connection mechanisms include a threaded connection in combination with an interlocking connection. The threaded connection members as described herein, can be made of any suitable material or materials. By providing at least two connection mechanisms, the multiple locking mechanism 34 provides a redundant connection between the first body portion 30 and the second body portion 35 that may reduce unwanted disconnection between the first body portion 30 and second body portion 35 during use.

The first body portion 30 and/or the second body portion 35 of the present invention are preferably manufactured from flexible tubings that are similar in construction to the tubings used in known catheters, the types of which are well described in the art. For example, the first body portion 30 and/or the second body portion 35 may be formed by extrusion of an organic polymer, typically a thermoplastic, such as nylon, polyethylene terephthalate (PET), polyvinyl-chloride (PVC), polyethylene, and the like. The first and/or second body portions can be reinforced or unreinforced, usually being reinforced by a metal braid which is laminated with a polymeric material. In one specific embodiment, the second body portion 35 may be a reusable shaft made of a memory shaped metal, i.e., flexible without plastic deformation, such as superelastic nitinol. Similarly, multiple locking mechanism 34 may preferably be made of a memory shaped metal such as nitinol. Nitinol is a nickel titanium alloy that can exhibit super-elasticity which is desirable in many situations. In some embodiments, the first body portion 30 may also be constructed of a memory shaped metal such as nitinol.

One illustrative embodiment of a multiple locking mechanism 34 of FIG. 1 is shown in greater detail in FIGS. 2, 3, 3A, 3B and 3C. FIG. 2 depicts a side view of multiple locking mechanism 34. Proximal end 40 of the first body portion (not shown) and distal end 56 of the second body portion (not shown), are connected by the multiple locking mechanism 34. At proximal end 40 is a first threaded connector 42 including a threaded portion 44. In one specific embodiment, threaded portion 44 is about 1.0 centimeters (cm) to about 2.0 cm long (axially) with a thread pitch of about 1.0 millimeters (mm) to about 1.5 mm. At distal end 56 is a second threaded connector 55 having a threaded portion (not shown). Threaded portion 44 of the first threaded connector 42 rotatably engages the threaded portion of the second threaded connecter 55. Once engaged, the first 42 and second 55 threaded connectors cooperate to connect the proximal end 40 of the first body portion to the distal end 56 of the second body portion. This provides one element of the multiple locking mechanism.

The second element of multiple locking mechanism 34 contains first interlocking element 41 at the proximal end 40 of the first body portion 30 and a second interlocking element 50 at the distal end 56 of the second body portion 35. When the first and second interlocking elements 41 and 50 interlock, the first and second body portions 30 and 35 are additionally secured.

As best seen in FIGS. 3–3C, second interlocking element 50 includes a latching portion 57. Latching portion 57 of second interlocking element 50 engages the first interlocking element 41 at the proximal end 40 of the first body portion as shown in FIG. 3A. As may be best seen in FIG. 3A, connection or disconnection of the body portions 30 and 35 would require outward deflection of second interlocking element 50 causing latching portion 57 to move outwardly over the raised interlocking element 41. Alternatively, the interlocking element 41 may deflect inward during connection/disconnection. In still another alternative, both second interlocking element 50 and first interlocking element 41 may deflect slightly during connection/disconnection.

It may be preferred that the interlocking elements 41 and 50 provide some axial tension to the threaded connectors 42 and 55 to assist in maintaining the connection between the first and second body portions 30 and 35. It may also be preferred that once the multiple locking mechanism is engaged, it should be able to withstand about 20 atmospheres to about 25 atmospheres without allowing disconnection between the catheter body portions 30 and 35.

FIG. 3B is a cross-sectional view of the proximal end 40 of the first body portion 33 illustrating the first lumen 48 and a guidewire lumen 49. Although the illustrated catheter include two lumens 48 and 49, catheters including multiple locking mechanisms according to the present invention may include as few as one lumen or three or more lumens depending on the intended use of the catheters.

FIG. 3C is a view of the distal end 56 of the second body portion 37 illustrating the first lumen 58 and a guidewire lumen 51 corresponding to lumens 48 and 49 as seen in FIG. 3B. FIG. 3C also shows an optional sealing ring 59. Sealing ring 59 preferably provides a secure seal when proximal end 40 of the first body portion 33 and distal end 56 of the second body portion are interlocked. It may be preferred that the sealing ring 59 seal the connection between lumens 48 and 58 sufficiently to withstand about 20 atmospheres to about 25 atmospheres when in use. The sealing ring 59 may be manufactured from any suitable material or materials.

Another illustrative embodiment of a multiple locking mechanism according to the present invention is illustrated in FIGS. 4 and 5. FIG. 4 depicts a side view of the multiple locking mechanism. Proximal end 140 of the first body portion (not shown) and distal end 156 of the second body portion (not shown), are connected by the multiple locking mechanism. At proximal end 140 is a first threaded connector 142 including a threaded portion 144. At distal end 156 is a second threaded connector 155 having a threaded portion (not shown). Threaded portion 144 of the first threaded connector 142 rotatably engages the threaded portion of the second threaded connecter 155. Once engaged, the first threaded connector 142 and the second threaded connector 155 cooperate to connect the proximal end 140 of the first body portion (not shown) to the distal end 156 of the second body portion (not shown). This provides one element of the multiple locking mechanism.

The second element of the multiple locking mechanism contains first interlocking element 141 having an annular depression at the proximal end 140 of the first body portion (not shown), and a second interlocking element 150 having a latching portion 157 at the distal end 156 of the second body portion (not shown). As best seen in FIG. 5, during connection, the interlocking element 150 preferably deflects outwardly until the latching portion 157 of element 150 mates with the annular depression provided by the first interlocking element 141. In some instances, the second interlocking element 150 may remain in deflection even when latching portion 157 is located in the annular depression of first interlocking element 141. When the first and second interlocking elements 141 and 150 interlock, the first and second body portions are additionally secured.

Figure 7:
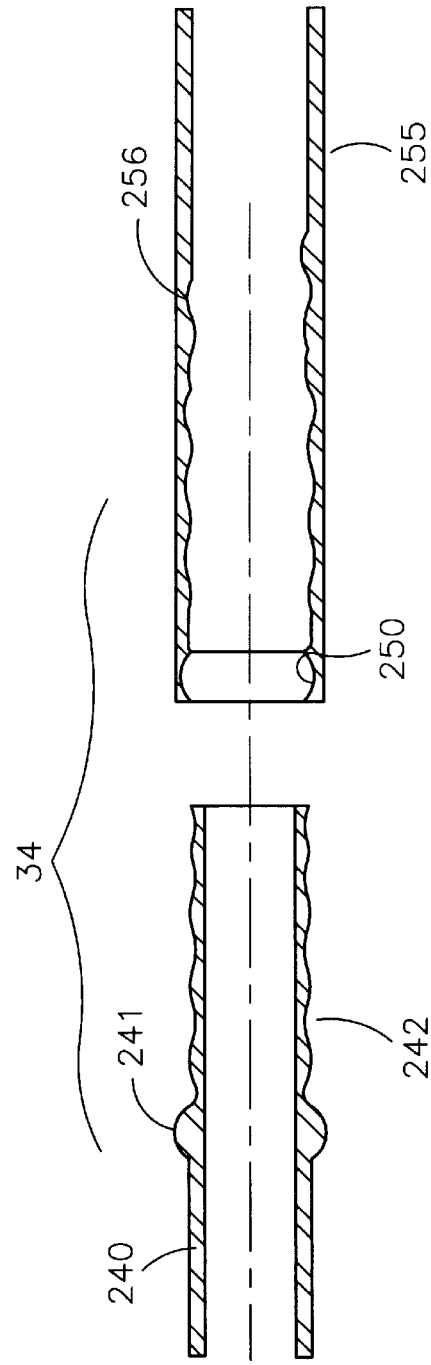
FIG. 7. is a cross-sectional view of the multiple locking mechanism shown in FIG. 6 taken along line 7—7 in FIG. 6.

Yet another illustrative embodiment of a multiple locking mechanism illustrated in FIGS. 6 and 7. FIG. 6 depicts a side view of the multiple locking mechanism. Proximal end 240 of the first body portion (not shown) and distal end 256 of the second body portion, are connected by the multiple locking mechanism 34. At proximal end 240 is a first threaded connector 242 including a threaded portion 244. At distal end 256 is a second threaded connector 255 having a threaded portion (not shown). Threaded portion 244 of the first threaded connector 242 rotatably engages the threaded portion of the second threaded connecter 255. Once engaged, the first threaded connector 242 and the second threaded connector 255 cooperate to connect the proximal end 240 of the first body portion 30 to the distal end 256 of the second body portion 35. This provides one element of the multiple locking mechanism.

The second element of the multiple locking mechanism contains first interlocking element 241 having an annular protrusion at the proximal end 240 of the first body portion (not shown) and a second interlocking element 250 comprising an annular depression at the distal end 256 of the second body portion (not shown). When the first and second interlocking elements 241 and 250 interlock, the first and second body portions are additionally secured.

As best seen in FIG. 7, first interlocking element 241 is a raised annular ring and second interlocking element 250 is a mating annular depression. Second interlocking element 250 engages the first interlocking element 241 at the proximal end 240 of the first body portion (not shown), by receiving the raised annular ring of element 241 in the annular depression of element 250. During connection/disconnection, one or both of the interlocking elements 241 and 250 deflect slightly as the parts mate with each other.

Thus, the present invention provides an intravascular catheter comprising a reusable shaft assembly having a multiple locking mechanism, preferably made of a memory shaped metal, such as nitinol, wherein the shaft assembly further provides a connection for an inflation device on the proximal end, and a connection for the balloon on the distal end. The distal portion, i.e., about the last 5.0 to about the last 10.0 cm., is preferably a disposable balloon which can be connected to the distal end of the proximal instrument. After the first dilatation, only the balloon head has to be changed to perform further dilatation. The proximal portion of the instrument can be sterilized and reused.

Although the invention has been described with particular reference to various embodiments thereof, variations and modifications of the present invention can be made within the contemplated scope of the following claims as is readily know to one skilled in the art.

What is claimed is:

1. A catheter body for an intravascular medical catheter, comprising:
    a first body portion comprising a first polymeric material, and proximal and distal ends and a first lumen extending from the proximal end to the distal end, at least portions of the first body portion being flexible and suitable for introduction into a blood passageway located within a patient;
    a second body portion comprising a second polymeric material, and proximal and distal ends and a second lumen extending from the proximal end to the distal end, at least portions of the second body portion being flexible and suitable for introduction into the blood passageway located within the patient;
    a multiple locking mechanism, comprising:
        a first threaded connector at the proximal end of the first body portion;
        a second threaded connector at the distal end of the second body portion, wherein the first and second threaded connectors cooperate to connect the proximal end of the first body portion to the distal end of the second body portion;
        a first interlocking element at the proximal end of the first body portion; and
        a second interlocking element at the distal end of the second body portion, wherein the first and second interlocking elements interlock when the first and second threaded connectors connect the first and second body portions together.

2. The intravascular catheter of claim 1, wherein the second body portion comprises a reusable shaft comprising a shape memory alloy.

3. The intravascular catheter of claim 2, wherein the shade memory alloy is nitinol.

4. The intravascular catheter of claim 1, wherein the first and second lumens are in fluid communication when the first and second body portions are interlocked.

5. The intravascular catheter as set forth in claim 4, further comprising a sealing ring between the first and second lumens.

6. The intravascular catheter as set forth in claim 1, wherein the first body portion further comprises a guidewire lumen extending from the proximal end to the distal end thereof, and wherein the second body portion further comprises a guidewire lumen, and further wherein the guidewire lumens of the first and second body portions are in fluid communication when the first and second body portions are interlocked.

7. The intravascular catheter as set forth in claim 1, wherein the first interlocking coupling element comprises a raised annular ring and the second interlocking element comprises a latching portion.

8. The intra-vascular catheter as set forth in claim 1, wherein the first interlocking coupling element comprises an annular depression and the second interlocking element comprises a latching portion.

9. The intravascular catheter as set forth in claim 1, wherein the first interlocking coupling element comprises a raised annular ring and the second interlocking element comprises an annular depression.

10. The intravascular catheter as set forth in claim 1, further comprising a work element disposed at the distal end of the first body portion.

11. The intravascular catheter as set forth in claim 10, wherein the work element is an expandable balloon.

12. The intra-vascular catheter as set forth in claim 1, wherein a proximal assembly comprising a perfusion or aspiration source is attached to the proximal end of the second body portion.

13. A method for assembling an at least partially flexible intravascular medical catheter suitable for introduction within a blood passageway of a patient, comprising:

providing a catheter, comprising:

a first body portion comprising a first polymeric material, and proximal and distal ends and a first lumen extending from the proximal end to the distal end, at least portions of the first body portion being flexible and suitable for introduction into a blood passageway located within a patient;

a second body portion comprising a second polymeric material, and proximal and distal ends and a second lumen extending from the proximal end to the distal end, at least portions of the second body portion being flexible and suitable for introduction into the blood passageway located within the patient;

a multiple locking mechanism, comprising:

a first threaded connector disposed at the proximal end of the first body portion;

a second threaded connector at the distal end of the second body portion, wherein the first and second threaded connectors cooperate to connect the proximal end of the first body portion to the distal end of the second body portion;

a first interlocking element disposed at the proximal end of the first body portion; and a second interlocking element disposed at the distal end of the second body portion, wherein the first and second interlocking elements interlock when the first and second threaded connectors connect the first and second body portions together;

connecting the first body portion with the second body portion by rotatably engaging the first and second threaded connectors;

interlocking the first and second interlocking elements; and placing the first and second lumens in fluid communication.

14. The method of claim 13, wherein placing the first and second lumens in fluid communication comprises providing a sealing ring between the first and second lumens.

15. The method of claim 13, wherein the first interlocking coupling element of the catheter comprises a raised annular ring and the second interlocking element comprises a latching portion, and further wherein interlocking the first and second interlocking elements comprises deflecting at least one of the raised annular ring and the latching portion.

16. The method of claim 15, wherein connection or disconnection of the first and second body portions provides an outward deflection of the second interlocking element.

17. The method of claim 13, wherein the first interlocking coupling element of the catheter comprises an annular depression and the second interlocking element comprises a latching portion, and further wherein interlocking the first and second interlocking elements comprises deflecting at least one of the annular depression and the latching portion.

18. The method of claim 13, wherein the first interlocking coupling element of the catheter comprises a raised annular ring and the second interlocking element comprises an annular depression, and further wherein interlocking the first and second interlocking elements comprises deflecting at least one of the raised annular ring and the annular depression.

19. The method of claim 13, wherein the first and second interlocking elements provide axial tension to the first and second threaded connectors when interlocked.

20. The method of claim 13, wherein the catheter further comprises a work element attached to the distal end of the first body portion.

* * * * *